United States Patent [19]

Diehr et al.

[11] Patent Number: 4,658,027

[45] Date of Patent: Apr. 14, 1987

[54] PROCESS FOR THE PREPARATION OF 1-(2-OXYAMINOSULPHONYL-PHENYL-SULPHONYL)-3-HETEROARYL-UREAS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld, all of Fed. Rep. of Germany

[73] Assignee: Bayer Aktiengesellschaft, Leverkusen, Fed. Rep. of Germany

[21] Appl. No.: 769,184

[22] Filed: Aug. 23, 1985

[30] Foreign Application Priority Data

Aug. 30, 1984 [DE] Fed. Rep. of Germany ....... 3431932

[51] Int. Cl.$^4$ ................. C07D 239/42; C07D 239/47; C07D 251/42; C07D 257/08

[52] U.S. Cl. ..................................... 544/321; 544/211; 544/182; 544/179; 544/208; 544/206; 544/332; 544/323; 544/327; 544/322; 544/320; 546/291; 546/305; 540/553

[58] Field of Search ................. 564/40; 546/334, 291, 546/309; 544/335, 211, 217, 218, 298, 326, 182, 179, 208, 197, 206, 332, 321, 323, 327; 260/330; 540/489

[56] References Cited

FOREIGN PATENT DOCUMENTS

| | | | |
|---|---|---|---|
| 0048143 | 3/1982 | European Pat. Off. | 564/40 |
| 0074282 | 3/1983 | European Pat. Off. | 564/40 |
| 0102925 | 3/1984 | European Pat. Off. | 564/40 |
| 0116518 | 8/1984 | European Pat. Off. | 564/40 |
| 0128274 | 12/1984 | European Pat. Off. | 564/40 |

OTHER PUBLICATIONS

Abstract of EP A3-0 085 028, Europe, published 8/3/83, "N–Phenylsulfonyl–N'–pyrimidinyl–und–triazinylharnstoffe".

*Primary Examiner*—Richard A. Schwartz
*Assistant Examiner*—Robert C. Whittenbaugh
*Attorney, Agent, or Firm*—Sprung Horn Kramer & Woods

[57] ABSTRACT

A process for the preparation of a 1-(2-oxyaminosulphonyl-phenylsulphonyl)-urea of the formula

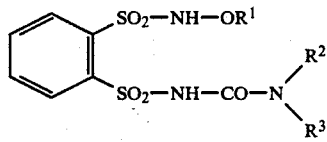

in which
R$^1$ is an optionally substituted radical from the series comprising alkyl, alkenyl, alkinyl, cycloalkyl, cycloalkylalkyl, aralkyl and aryl,
R$^2$ is hydrogen or an optionally substituted radical from the series comprising alkyl, alkenyl, alkinyl and aralkyl, and
R$^3$ is an optionally substituted and/or optionally fused six-membered aromatic heterocyclic radical containing at least one nitrogen atom, comprising reacting water with a benzodisultam of the formula

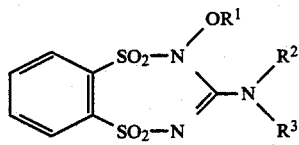

at a temperature between 0° C. and 100° C. The products are herbicidally active.

4 Claims, No Drawings

PROCESS FOR THE PREPARATION OF 1-(2-OXYAMINOSULPHONYL-PHENYLSULPHONYL)-3-HETEROARYL-UREAS

The invention relates to a new process for the preparation of 1-(2-oxyaminosulphonyl-phenyl-sulphonyl)-3-heteroaryl-ureas.

It is known that certain 1-(2-oxyaminosulphonyl-phenylsulphonyl)-3-heteroaryl-ureas, such as, for example, 1-(2-[N-methoxy-N-methyl-aminosulphonyl]-phenylsulphonyl)-3-(4,6-dimethoxy-pyrimidin-2-yl)-urea, are obtained by reacting 2-oxyaminosulphonyl-phenylsulphonyl isocyanates, such as, for example, 2-(N-methoxy-N-methyl-aminosulphonyl)-phenylsulphonyl isocyanate, with heteroarylamines, such as, for example, 2-amino-4,6-dimethoxy-pyrimidine (compare U.S. Pat. No. 4,310,346). However, synthesis of 1-(2-oxyaminosulphonyl-phenylsulphonyl)-3-heteroaryl-ureas with an NH grouping in the oxyaminosulphonyl radical has not yet been successful by the method mentioned.

A new process has now been found for the preparation of 1-(2-oxyaminosulphonyl-phenylsulphonyl)-3-heteroaryl-ureas of the general formula (I)

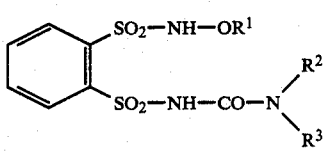

in which
R$^1$ represents an optionally substituted radical from the series comprising alkyl, alkenyl, alkinyl, cycloalkyl, cycloalkylalkyl, aralkyl and aryl,
R$^2$ represents hydrogen or an optionally substituted radical from the series comprising alkyl, alkenyl, alkinyl and aralkyl and
R$^3$ represents an optionally substituted and/or optionally fused six-membered aromatic heterocyclic radical containing at least one nitrogen atom,
which is characterized in that benzodisultams of the formula (II)

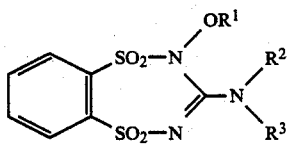

in which
R$^1$, R$^2$ and R$^3$ have the abovementioned meanings, are reacted with water, if appropriate in the presence of bases and if appropriate in the presence of diluents, at temperatures between 0° C. and 100° C.

It is to be regarded as surprising that the 1-(2-oxyaminosulphonyl-phenylsulphonyl)-3-heteroaryl-ureas of the formula (I) can be prepared by the process according to the invention by selective ring-opening of benzodisultams of the formula (II), since other cleavage reactions, for example by attack on the sulphonyl groupings, were also to be expected, in addition to this novel reaction.

The chemical reaction which proceeds in the process according to the invention can be outlined, for example, by the following equation:

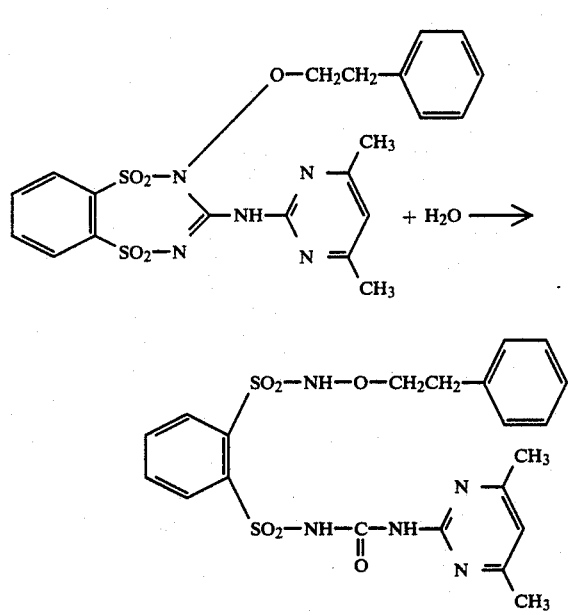

Formula (II) provides a definition of the benzodisultams to be used as starting substances.

Preferably, in this formula,
R$^1$ represents C$_1$-C$_{12}$-alkyl [which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkylcarbonyl, C$_1$-C$_4$-alkoxy-carbonyl, C$_1$-C$_4$-alkylamino-carbonyl or di-(C$_1$-C$_4$-alkyl)-amino-carbonyl], or represents C$_3$-C$_6$-alkenyl, C$_3$-C$_6$-alkinyl, C$_3$-C$_6$-cycloalkyl, C$_3$-C$_6$-cycloalkyl-C$_1$-C$_2$-alkyl, phenyl-C$_1$-C$_2$-alkyl [which is optionally substituted by fluorine, chlorine, nitro, cyano, C$_1$-C$_4$-alkyl, C$_1$-C$_4$-alkoxy or C$_1$-C$_4$-alkoxycarbonyl], or represents phenyl [which is optionally substituted by fluorine, chlorine, nitro, cyano, C$_1$-C$_4$-alkyl, trifluoromethyl, C$_1$-C$_4$-alkoxy, C$_1$-C$_2$-fluoroalkoxy, C$_1$-C$_4$-alkylthio. trifluoromethylthio or C$_1$-C$_4$-alkoxycarbonyl], R$^2$ represents hydrogen or C$_1$-C$_4$-alkyl [which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-aminocarbonyl], or represents C$_3$-C$_6$-alkenyl, C$_3$-C$_6$-alkinyl or phenyl-C$_1$-C$_2$-alkyl [which is optionally substituted by fluorine, chlorine, nitro, cyano, C$_1$-C$_4$-alkyl, C$_1$-C$_4$-alkoxy or C$_1$-C$_4$-alkoxy-carbonyl] and
R$^3$ represents the radical

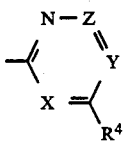

wherein

R⁴ represents hydrogen, fluorine, chlorine, bromine, hydroxyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino, $C_1$–$C_4$-alkylamino or di($C_1$–$C_4$-alkyl)-amino, X represents nitrogen or a methine bridge (CH), Y represents nitrogen or an optionally substituted methine bridge C—$R^5$, wherein $R^5$ represents hydrogen, fluorine, chlorine, bromine or $C_1$–$C_4$-alkyl, and Z represents nitrogen or an optionally substituted methine bridge C—$R^6$, wherein $R^6$ represents hydrogen, fluorine, chlorine, bromine, hydroxyl, $C_1$–$C_4$-alkyl [which is optionally substituted by fluorine and/or chlorine], $C_1$–$C_4$-alkoxy [which is optionally substituted by fluorine and/or chlorine], $C_1$–$C_4$-alkylthio [which is optionally substituted by fluorine and/or chlorine], amino, $C_1$–$C_4$-alkylamino or di($C_1$–$C_4$-alkyl)-amino.

Particularly preferred starting substances of the formula (II) are those in which $R^1$ represents $C_1$–$C_8$-alkyl [which is optionally substituted by fluorine or chlorine], $C_3$–$C_4$-alkenyl, $C_1$–$C_2$-alkoxy-carbonylmethyl, phenethyl or benzyl [which is optionally substituted by fluorine, chlorine, nitro, cyano, methyl, methoxy or methoxy-carbonyl], $R^2$ represents hydrogen and $R^3$ represents the radical

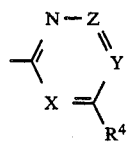

wherein $R^4$ represents chlorine, methyl, methoxy or ethoxy,

X represents nitrogen,

Y represents a methine bridge (CH) and

Z represents an optionally substituted methine bridge C—$R^6$, wherein $R^6$ represents hydrogen, chlorine, methyl, methoxy, ethoxy, methylthio, ethylthio, dimethylamino or diethylamino.

Examples of starting substances of the formula (II) are listed in the following Table 1:

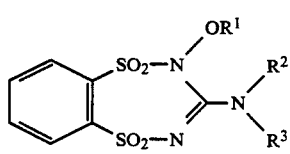

TABLE 1

Examples of starting substances of the formula (II)

| $R^1$ | $R^2$ | $R^3$ |
|---|---|---|
| —$C_5H_{11}$ | H | ![pyrimidine with 2 CH3] |
| —$C_8H_{17}$ | H | ![pyrimidine with 2 CH3] |
| —$CH_2$—⌬ | H | ![pyrimidine with 2 CH3] |
| —$CH_2$—CH=$CH_2$ | H | ![pyrimidine with 2 CH3] |
| —$CH_2CH_2$—⌬ | H | ![pyrimidine with 2 CH3] |
| —$CH_2$—⌬—$CH_3$ | H | ![pyrimidine with 2 CH3] |
| —$CH_2$—⌬(Cl) | H | ![pyrimidine with 2 CH3] |
| —$CH_2$—⌬—$NO_2$ | H | ![pyrimidine with 2 CH3] |

TABLE 1-continued
Examples of starting substances of the formula (II)

| $R^1$ | $R^2$ | $R^3$ |
|---|---|---|
| 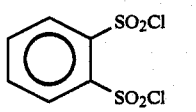 | H | 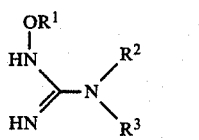 |

The compounds of the formula (II) are described in Application Ser. No. 769,191, filed Aug. 23, 1985 now pending, corresponding to German Application No. P34 31 922.0, filed Aug. 30, 1984 (LeA 23 257). The compounds of the formula (II) are obtained by a process in which benzen-1,2-disulphonic acid dichloride of the formula (III)

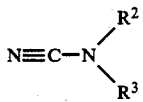 (III)

is reacted with oxyguanidine derivatives of the formula (IV)

 (IV)

in which

R$^1$, R$^2$ and R$^3$ have the abovementioned meaning, in the presence of acid acceptors, such as, for example, pyridine or diazabicyclooctane (DABCO), and, if appropriate, in the presence of diluents, such as, for example, methylene chloride, chloroform, tetrahydrofuran or dioxane, at temperatures between −30° C. and +50° C.

Working up can be effected by customary methods, for example by concentrating the mixture, taking up the residue in methylene chloride, washing the mixture with dilute hydrochloric acid and with water and separating off, drying, filtering and concentrating the organic phase, the products of the formula (II) remaining in the residue.

The benzene-1,2-disulphonic acid dichloride of the formula (III) to be used as the starting substance is already known (compare J.Org.Chem. 31, (1966), 3289-3292).

Formula (IV) provides a general definition of the oxyguanidine derivatives also to be used as starting substances. In formula (IV), R$^1$, R$^2$ and R$^3$ preferably and particularly have the same meanings as are given above as preferred or as particularly preferred in the context of the definition of the substituents of formula (II).

Examples which may be mentioned of starting substances of the formula (IV) are: N'-(4-methyl-pyrimidin-2-yl)-, N'-(4,6-dimethyl-pyrimidin-2-yl)-, N'-(4-methoxy-6-methyl-pyrimidin-2-yl)-, N'-(4-ethoxy-6-methyl-pyrimidin-2-yl)-, N'-(4-chloro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthio-pyrimidin-2-yl)- and N'-(4-dimethylamino-6-methyl-pyrimidin-2-yl)-N'''-methoxy-guanidine, -N'''-ethoxy-guanidine, -N'''-propoxy-guanidine, -N'''-isopropoxyguanidine, -N'''-butoxy-guanidine, -N'''-isobutoxy-guanidine, -N'''-sec.-butoxy-guanidine, -N'''-pentoxy-guanidine, -N'''-isopentoxy-guanidine, -N'''-hexyloxy-guanidine, -N'''-octyloxy-guanidine, -N'''-allyloxy-guanidine, -N'''-(2-chloro-ethoxy)-guanidine, -N'''-(2-fluoro-ethoxy)-guanidine, -N'''-(2-chloro-propoxy)-guanidine, -N'''-(2-fluoro-propoxy)-guanidine, -N'''-(3-chloro-propoxy)-guanidine, -N'''-(4-chlorobutoxy)-guanidine, -N'''-methoxycarbonylmethoxy-guanidine, -N'''-ethoxycarbonylmethoxy-guanidine, -N'''-(1-methoxycarbonyl-ethoxy)-guanidine, -N'''-(1-ethoxycarbonylethoxy)-guanidine, -N'''-dimethylaminocarbonylmethoxy-guanidine, -N'''-(2-phenyl-ethoxy)-guanidine, -N'''-phenoxy-guanidine, -N'''-(4-methyl-benzyloxy)-guanidine, -N'''-(4-fluorobenzyloxy)-guanidine, -N'''-(4-chloro-benzyloxy)-guanidine, -N'''-(4-nitrobenzyloxy)-guanidine, -N'''-(2,6-dichlorobenzyloxy)-guanidine, -N'''-(4-methoxycarbonyl-benzyloxy)-guanidine and -N'''-(4-ethoxycarbonyl-benzyloxy)-guanidine.

The starting substances of the formula (IV) are known in some cases (compare J.Chem.Soc. 1962, 3915); some of them are the subject of commonly assigned Application Ser. No. 578,345, filed Feb. 9, 1984, now pending, corresponding to DE-OS (German Published Specification) No. 3,334,455.

The compounds of the formula (IV) are obtained by a process in which cyanamide derivatives of the formula (V)

 (V)

in which

R$^2$ and R$^3$ have the abovementioned meanings, are reacted with hydroxylamine derivatives of the formula (VI)

$$H_2N-OR^1 \quad (VI)$$

in which

R$^1$ has the abovementioned meaning, or with hydrochlorides of hydroxylamine derivatives of the formula (VI), if appropriate in the presence of diluents, such as, for example, ethanol, propanol or butanol, at temperatures between 20° C. and 120° C. and, if appropriate, the reaction produces are treated with acid acceptors, such as, for example, ammonia, potassium carbonate or sodium hydroxide.

The cyanamide derivatives of the formula (V) are known in some cases (compare J. Chem. Soc. 1953, 1725). The compounds of the formula (V) are essentially obtained by the following synthesis routes:

(a) by reaction of alkali metal or alkaline earth metal salts of cyanamide—such as, for example, sodium cyanamide or calcium cyanamide—with chloro-hetarenes of the formula (VII)

$$Cl-R^3 \quad (VII)$$

in which

R$^3$ has the abovementioned meaning, and, if appropriate, subsequently—if R$^2$ does not represent hydrogen—with halogen compounds of the formula (VIII)

$$Q-R^2 \quad (VIII)$$

in which
R² represents an optionally substituted radical from the series comprising alkyl, alkenyl, alkinyl and aralkyl and
Q represents chlorine, bromine or iodine,
if appropriate in the presence of inert diluents, such as, for example, acetone, acetonitrile or dimethylformamide, at temperatures between 0° C. and 100° C.

After the mixture has been concentrated and the residue has been dissolved in water, the cyanamide derivatives of the formula (V) can be precipitated by acidification, for example with hydrochloric acid, and isolated by filtration with suction.

Alternatively, the compounds of the formula (V) are obtained (b) in the case where R³ represents a substituted pyrimidinyl radical, by reaction of cyanoguanidine ("dicyandiamide") with β-dicarbonyl compounds, such as acetylacetone (compare J. Chem. Soc. 1953, 1725–1730), acetoacetic acid esters (compare J. Prakt. Chem. 77 (1908), 542 and J. Chem. Soc. 1948, 586) or malonic acid esters (compare German Patent Specification No. 158,591).

The 2-cyanoamino-4-hydroxy-6-methyl- or -4,6-dihydroxy-pyrimidines obtained from acetoacetic acid esters or malonic acid esters can be converted into corresponding 2-cyanoamino-4-alkoxy-6-methyl- or -4,6-dialkoxy-pyrimidines in a known manner by reaction with alkylating agents, such as, for example, dimethyl sulphate or diethyl sulphate, if appropriate in the presence of diluents, such as, for example, water, methanol, ethanol, n- or iso-propanol, acetone, dioxane or dimethylformamide, and in the presence of acid-binding agents, such as, for example, sodium hydroxide or potassium hydroxide or sodium carbonate or potassium carbonate. To avoid N-alkylation, acylation is carried out, if appropriate, with an acylating agent, such as, for example, acetic anhydride or acetyl chloride, and, after the alkylation, the product is deacylated again with aqueous acids or bases.

In another alternative process, the compounds of the formula (V) are obtained by a procedure in which (c) amino-hetarenes of the formula (IX)

$$H_2N-R^3 \quad (IX)$$

in which
R³ has the abovementioned meaning, are reacted with carbonyl isothiocyanates of the formula (X)

$$R^7-\overset{O}{\underset{\|}{C}}-N=C=S \quad (X)$$

in which
R⁷ represents ethoxy or phenyl,
if appropriate in the presence of an inert diluent, such as, for example, acetone, acetonitrile or toluene, at temperatures between 0° C. and 100° C., the carbonylthioureas thereby formed, of the formula (XI)

$$R^7-\overset{O}{\underset{\|}{C}}-NH-\overset{S}{\underset{\|}{C}}-NH-R^3 \quad (XI)$$

in which
R³ and R⁷ have the abovementioned meaning,
are isolated by filtration with suction, if necessary after concentration in the mixture, and are reacted with aqueous alkali metal or alkaline earth metal hydroxide solution, such as, for example, sodium hydroxide solution, if appropriate in the presence of an organic solvent, such as, for example, tetrahydrofuran or dioxane, at temperatures between 0° C. and 120° C., and the thioureas obtained as crystals after acidification, for example with hydrochloric acid, of the formula (XII)

$$H_2N-\overset{S}{\underset{\|}{C}}-NH-R^3 \quad (XII)$$

in which
R³ has the abovementioned meaning,
are isolated by filtration with suction and reacted with metal compounds which can bond hydrogen sulphide, such as, for example, with lead-II acetate, copper-II acetate, mercury-II acetate or iron-II acetate, in the presence of aqueous alkali metal or alkaline earth metal hydroxide solutions, such as, for example, sodium hydroxide solution, at temperatures between 20° C. and 100° C., and, when the reaction has ended, the mixture is filtered and the filtrate is acidified with an acid, such as, for example, acetic acid. The products of the formula (V) thereby obtained as crystals can be isolated by filtration with suction.

The starting substances for the preparation processes described above under (a), (b) and (c) for the cyanamide derivatives of the formula (V) are known and/or can be prepared by processes which are known per se.

These substances include the chloro-hetarenes of the formula (VII) (compare J. Chem. Soc. (c) 1966, 2031; Chem. Pharm. Bull. 11 (1963), 1382–1388 and Arch. Pharm. 295 (1962), 649–657), the halogen compounds of the formula (VIII) (commercially available chemicals), the amino-hetarenes of the formula (IX) (compAre Chem. Pharm. Bull. 11, (1963), 1382–1388; J. Chem. Soc. 1946, 81 and U.S. Pat. No. 4,299,960) and the carbonyl isothiocyanates of the formula (X) (compare J. Heterocycl. Chem. 5 (1968), 837 and U.S. Pat. No. 4,160,037).

The process according to the invention is preferably carried out in water as the solvent. Other possible diluents are all the inert organic solvents, but preferably aprotic polar solvents. These include ketones, such as, for example, acetone and methyl ethyl ketone, nitriles, such as, for example, acetonitrile and propionitrile, dimethylsulphoxide, sulpholane, 1,2-dimethoxyethane and dioxane.

The process according to the invention is preferably carried out in the presence of bases. Preferred possible bases are alkali metal and alkaline earth metal hydroxides, such as, for example, sodium hydroxide, potassium hydroxide and calcium hydroxide, and tertiary amines, such as, for example, pyridine or diazabicyclooctane (DABCO).

The reaction temperatures can be varied within a substantial range in the process according to the invention. The reaction is in general carried out between 0°

C. and +100° C., preferably between 10° C. and +80° C. The process according to the invention is in general carried out under normal pressure.

For carrying out the process according to the invention, in general between 1 and 100 moles, preferably between 5 and 50 moles, of water and, if appropriate, between 1 and 10 moles, preferably between 1 and 5 moles, of a base are employed per mole of benzodisultam of the formula (II).

The reaction components are usually brought together at room temperature and the reaction mixture is stirred until the reaction has ended.

Working up can be carried out in the usual manner; for example by acidifying the mixture—for example with hydrochloric acid—and concentrating it to about half the volume, and isolating the product of the formula (I) obtained as crystals by filtration with suction.

The 1-(2-oxyaminosulphonyl-phenylsulphonyl)-3-heteroaryl-ureas of the formula (I) to be prepared by the process according to the invention can be used as herbicides (compare Application Ser. No. 769,224, filed Aug. 23, 1985, now pending, corresponding to Japanese Patent Application No. Sho. 59-21839 of Feb. 10, 1984 and the German Patent Application No., filed at the same time, P 34 31 929.8 (LeA 23 311); the compound which can be prepared according to the following Example 1 shows a particularly good herbicidal action).

PREPARATION EXAMPLES

Example 1

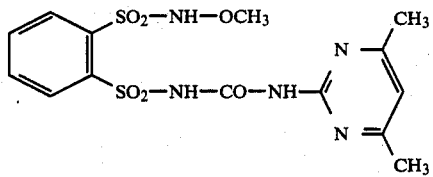

10.8 g (0.027 mole) of the compound of the following structural formula

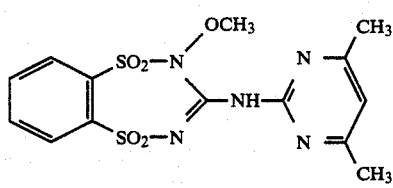

are added in portions to a solution of 4.0 g (0.1 mole) of sodium hydroxide in 100 ml of water at 20° C., with stirring. The reaction mixture is stirred until a clear solution has formed and is then acidified with concentrated hydrochloric acid. The product thereby obtained as crystals is isolated by filtration with suction.

9.5 g (90% of theory) of 1-(2-methoxy-aminosulphonyl-phenylsulphonyl)-3-(4,6-dimethyl-pyrimidin-2-yl)-urea of melting point 218° C. are obtained.

The same result is obtained if, instead of water, mixtures of water with acetonitrile, dioxane or tetrahydrofuran are used as the diluent.

The compounds of the formula (I) listed in the following Table 2 can be prepared analogously:

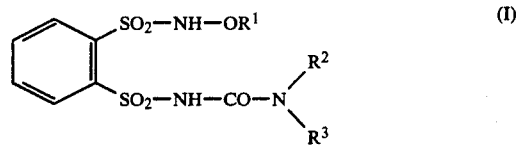

TABLE 2

| Example No. | $R^1$ | $R^2$ | $R^3$ | Melting Point (°C.) |
|---|---|---|---|---|
| 2 | —C$_4$H$_9$—n | H | 4,6-dimethylpyrimidin-2-yl | 169 |
| 3 | —C$_3$H$_7$—n | H | 4,6-dimethylpyrimidin-2-yl | 212 (decomposition) |
| 4 | —CH(CH$_3$)$_2$ | H | 4,6-dimethylpyrimidin-2-yl | 218 (decomposition) |
| 5 | —C$_8$H$_{17}$—n | H | 4,6-dimethylpyrimidin-2-yl | 145 |
| 6 | —CH$_2$—C$_6$H$_5$ | H | 4,6-dimethylpyrimidin-2-yl | 188 |
| 7 | —CH$_2$—CH=CH$_2$ | H | 4,6-dimethylpyrimidin-2-yl | 182 (decomposition) |
| 8 | —C$_2$H$_5$ | H | 4,6-dimethylpyrimidin-2-yl | 218 |

TABLE 2-continued

| Example No. | R¹ | R² | R³ | Melting Point (°C.) |
|---|---|---|---|---|
| 9 | —CH₃ | H | 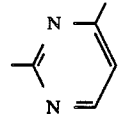 4,6-dimethylpyrimidin-2-yl | 194–195 |
| 10 | —CH₃ | H | 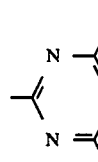 4-methyl-6-methoxypyrimidin-2-yl | 218 |

PREPARATION OF THE STARTING COMPOUNDS OF THE FORMULA (II)

Example (II-1)

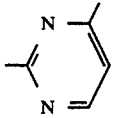

14 g (0.05 mole) of benzene-1,2-disulphonic acid chloride are added in portions to a mixture of 13.6 g (0.05 mole) of N'-(4,6-dimethylpyrimidin-2-yl)-N''-benzyloxy-guanidine, 12 g (0.15 mole) of pyridine and 100 ml of methylene chloride at −20° C. The mixture is subsequently stirred at −20° C. for 3 hours and at +20° C. for 15 hours.

The reaction mixture is then evaporated and 70 ml of dioxane are added to the residue. The mixture is filtered. The filtrate is concentrated, the residue is triturated with ethanol and the product precipitated is isolated by filtration with suction.

15 g (68% of theory) of the compound of the above-mentioned structural formula of melting point 199° C. are obtained.

The compounds of the formula (IIa) listed in the following Table 3 can be prepared analogously:

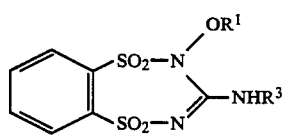  (IIa)

TABLE 3

| Example No. | R¹ | R³ | Melting Point (°C.) |
|---|---|---|---|
| (II-2) | —C₈H₁₇ | 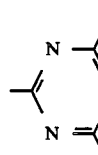 | 164 |
| (II-3) | —CH₂CH₂—C₆H₅ | 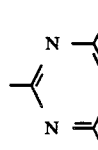 | |
| (II-4) | —CH₃ | 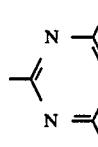 | 158 |
| (II-5) | —C₂H₅ | 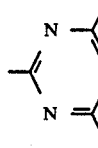 | 104 (decomposition) |
| (II-6) | —C₃H₇(—n) | 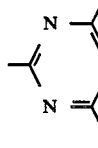 | 134 |
| (II-7) | —C₃H₇(—i) | 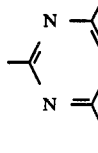 | amorphous |
| (II-8) | —C₄H₉(—n) | 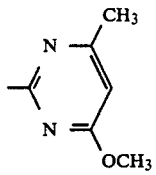 | 179 |
| (II-9) | —CH₂—CH=CH₂ | 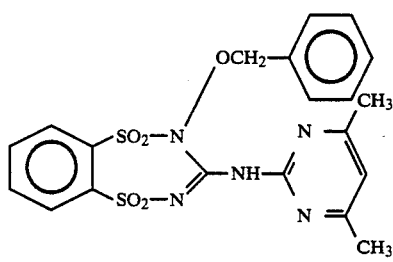 | 180 (decomposition) |

TABLE 3-continued

| Example No. | R¹ | R³ | Melting Point (°C.) |
|---|---|---|---|
| (II-10) | —CH₂—COOC₂H₅ | 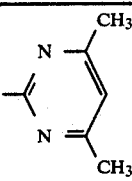 | 210 (decomposition) |
| (II-11) | —CH₃ | 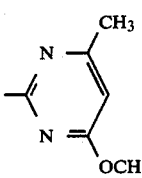 | 151 |
| (II-12) | —CH₃ | 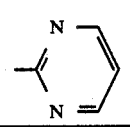 | 187 (decomposition) |

PREPARATION OF THE STARTING SUBSTANCES OF THE FORMULA (IV)

Example (IV-1)

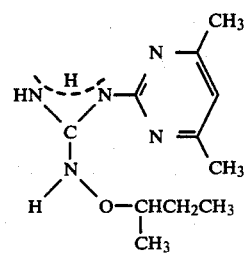

A mixture of 143 g (0.97 mole) of 2-cyanoamino-4,6-dimethyl-pyrimidine, 94.3 g (1.06 mole) of O-sec.-butyl-hydroxylamine and 190 ml of ethanol is heated at the boiling point under reflux for 6 hours. The mixture is then filtered with suction, the filtrate is concentrated and 500 ml of water are added to the residue. The product thereby obtained as crystals is isolated by filtration with suction.

131 g (57% of theory) of N'-(4,6-dimethyl-pyrimidin-2-yl)-N''-sec.-butoxy-guanidine of melting point 78° C. are obtained.

The compounds of the formula (IV) listed in the following Table 4 can be prepared analogously:

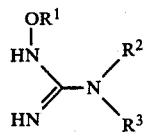 (IV)

TABLE 4

| Example No. | R¹ | R² | R³ | Melting point (°C.) |
|---|---|---|---|---|
| (IV-2) | —CH₂CH(CH₃)₂ | H | 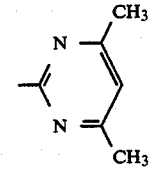 | 52 |
| (IV-3) | —CH₂CH=CH₂ | H | 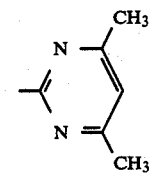 | 103 |
| (IV-4) | —CH₂CH₂—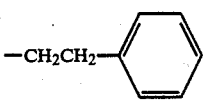 | H | 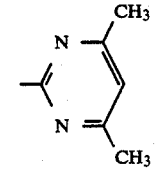 | $n_D^{24} = 1.5776$ |

TABLE 4-continued

| Example No. | R[1] | R[2] | R[3] | Melting point (°C.) |
|---|---|---|---|---|
| (IV-5) | —C$_8$H$_{17}$n | H | 4,6-dimethylpyrimidin-2-yl | 58 |
| (IV-6) | —CH$_2$—(2-chlorophenyl) | H | 4,6-dimethylpyrimidin-2-yl | 102–103 |
| (IV-7) | —CH$_2$CH$_2$CH$_2$Cl | H | 4,6-dimethylpyrimidin-2-yl | 137 |
| (IV-8) | phenyl | H | 4,6-dimethylpyrimidin-2-yl | 189–192 (decomposition) |
| (IV-9) | —CH$_2$COOCH$_3$ | H | 4,6-dimethylpyrimidin-2-yl | 148–149 |
| (IV-10) | —CH$_2$COOC$_2$H$_5$ | H | 4,6-dimethylpyrimidin-2-yl | 98–99 |
| (IV-11) | —CH(CH$_3$)COOCH$_3$ | H | 4,6-dimethylpyrimidin-2-yl | 147–148 |
| (IV-12) | —CH$_2$—(4-methylphenyl) | H | 4,6-dimethylpyrimidin-2-yl | 85–86 |

TABLE 4-continued

| Example No. | R$^1$ | R$^2$ | R$^3$ | Melting point (°C.) |
|---|---|---|---|---|
| (IV-13) | -CH$_2$-(2-F-C$_6$H$_4$) | H | 4,6-dimethylpyrimidin-2-yl | 114–116 |
| (IV-14) | cyclohexyl | H | 4,6-dimethylpyrimidin-2-yl | |
| (IV-15) | -CH$_2$-cyclohexyl | H | 4,6-dimethylpyrimidin-2-yl | |
| (IV-16) | -CH$_2$CON(CH$_3$)$_2$ | H | 4,6-dimethylpyrimidin-2-yl | |
| (IV-17) | -CH$_2$OCH$_3$ | H | 4,6-dimethylpyrimidin-2-yl | |
| (IV-18) | -CH$_2$SCH$_3$ | H | 4,6-dimethylpyrimidin-2-yl | |
| (IV-19) | -CH$_2$-(4-COOC$_2$H$_5$-C$_6$H$_4$) | H | 4,6-dimethylpyrimidin-2-yl | 138 |
| (IV-20) | -CH$_2$CF$_3$ | H | 4,6-dimethylpyrimidin-2-yl | |

TABLE 4-continued

| Example No. | R¹ | R² | R³ | Melting point (°C.) |
|---|---|---|---|---|
| (IV-21) | —CH₂—(2,6-dichlorophenyl) | H | 4,6-dimethylpyrimidin-2-yl | 140–145 |
| (IV-22) | —CH₂—(4-nitrophenyl) | H | 4,6-dimethylpyrimidin-2-yl | 170–2 |
| (IV-23) | —CH₂—phenyl | H | 4,6-dimethylpyrimidin-2-yl | 102 |
| (IV-24) | CH₃ | CH₃ | 4,6-dimethylpyrimidin-2-yl | 95 |
| (IV-25) | CH₃ | CH₃ | 4,6-dimethoxypyrimidin-2-yl | 135 |
| (IV-26) | CH₃ | H | 4,6-dimethoxypyrimidin-2-yl | 122 |
| (IV-27) | CH₃ | H | 4-methylpyrimidin-2-yl | 152 |
| (IV-28) | CH₃ | H | 4-methoxy-6-methylpyrimidin-2-yl | 126 |
| (IV-29) | CH₃ | H | 4-methoxy-6-(diethylamino)-1,3,5-triazin-2-yl | 112 |

TABLE 4-continued

| Example No. | R¹ | R² | R³ | Melting point (°C.) |
|---|---|---|---|---|
| (IV-30) | CH₃ | H | pyrimidine with SCH₃ and NHC₂H₅ substituents | 117 |
| (IV-31) | —CH(CH₃)₂ | H | 4,6-dimethylpyrimidin-2-yl | 84 |
| (IV-32) | —C₄H₉(n) | H | 4,6-dimethylpyrimidin-2-yl | oil |
| (IV-33) | —C₃H₇(—n) | H | 4,6-dimethylpyrimidin-2-yl | oil |
| (IV-34) | —CH₂—COOC₃H₇(—i) | H | 4,6-dimethylpyrimidin-2-yl | 112 |
| (IV-35) | —C₂H₅ | H | 4,6-dimethylpyrimidin-2-yl | 88 |
| (IV-36) | —CH₃ | H | 4-methyl-6-(N(C₂H₅)₂)pyrimidin-2-yl | 112 |
| (IV-37) | —CH₂—CH(CH₃)₂ | H | 4,6-dimethoxypyrimidin-2-yl | 76 |

TABLE 4-continued

| Example No. | R¹ | R² | R³ | Melting point (°C.) |
|---|---|---|---|---|
| (IV-38) | −CH(CH₃)−C₂H₅ | H | pyrimidine with 4-OCH₃, 2-, 6-OCH₃ | 68 |
| (IV-39) | −C₂H₅ | H | pyrimidine with 4-CH₃ | 95 |
| (IV-40) | −CH₃ | H | pyrimidine with 4-C₂H₅ | 98 |
| (IV-41) | −CH₃ | H | pyrimidine with 4-OCH₃, 6-Cl | 112 |
| (IV-42) | −CH₃ | H | pyrazine with CH₃, CH₃ | 143 |
| (IV-43) | −CH₃ | H | pyrimidine with 4-CH₃, 6-CH₃ | 110 |
| (IV-44) | −CH₂−COOC₂H₅ | H | pyrimidine with 4-CH₃ | — |
| (IV-45) | −CH₂−(2-Cl-C₆H₄) | H | pyrimidine with 4-CH₃ | 140 |
| (IV-46) | −CH₂−C₆H₅ | H | pyrimidine with 4-CH₃ | 150 |
| (IV-47) | −CH₂−(2-F-C₆H₄) | H | pyrimidine with 4-CH₃ | 205 |

TABLE 4-continued

| Example No. | R¹ | R² | R³ | Melting point (°C.) |
|---|---|---|---|---|
| (IV-48) | —CH₂—CH=CH₂ | H | 4,6-dimethylpyrimidin-2-yl | |
| (IV-49) | —C₄H₉(—n) | H | 4,6-dimethylpyrimidin-2-yl | |
| (IV-50) | —C₄H₉(—s) | H | 4,6-dimethylpyrimidin-2-yl | |
| (IV-51) | —CH₂CH₂CH₂—Cl | H | 4,6-dimethylpyrimidin-2-yl | ~102 |
| (IV-52) | —CH₃ | H | 4,6-diethoxypyrimidin-2-yl | |
| (IV-53) | —CH₃ | H | pyrimidin-2-yl | 107–109 |
| (IV-54) | —CH₂—C₆H₅ | H | 4,6-dimethoxypyrimidin-2-yl (with CH₃ shown) | $n_D^{20} = 1.5645$ |
| (IV-55) | —CH₂—C₆H₅ | H | 4-ethylpyrimidin-2-yl | 112 |
| (IV-56) | —CH₂—C₆H₅ | H | 4,6-dimethoxypyrimidin-2-yl | 74 |
| (IV-57) | —CH₂—C₆H₅ | H | 4-methylthio-6-ethylaminopyrimidin-2-yl | 122 |

TABLE 4-continued

| Example No. | R¹ | R² | R³ | Melting point (°C.) |
|---|---|---|---|---|
| (IV-58) | —$C_8H_{17}$(—n) | H | pyrimidine with $CH_3$ and $OCH_3$ | 95 |
| (IV-59) | —$CH_2$—phenyl | H | pyrimidine with $CH_3$ and $OCH_3$ | 112 |
| (IV-60) | —$CH_2CH_2CH_2CH_2$—Cl | H | pyrimidine with $CH_3$ and $CH_3$ | oil |
| (IV-61) | —$CH_2$—$CH_2$—Cl | H | pyrimidine with $CH_3$ and $CH_3$ | oil |
| (IV-62) | —CH(—phenyl)$_2$ | H | pyrimidine with $CH_3$ and $CH_3$ | 165 |

PREPARATION OF THE STARTING SUBSTANCES OF THE FORMULA (V)

Example (V-1)

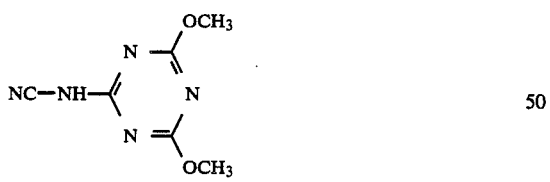

52.7 g (0.3 mole) of 2-chloro-4,6-dimethoxy-s-triazine are added to a solution of 30 g (0.3 mole) of the disodium salt of cyanamide in 600 ml of acetone, and the reaction mixture is heated at the boiling point under reflux for 6 hours. After the solvent has been distilled off, the crystalline residue is dissolved in 250 ml of water and the solution is acidified with concentrated hydrochloric acid. The product obtained as crystals is isolated by filtration with suction.

33 g (61% of theory) of 2-cyanoamino-4,6-dimethoxy-s-triazine with a melting point above 300° C. are obtained.

Example (V-2)

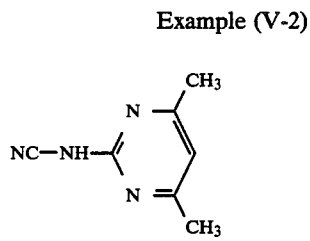

A mixture of 42 g (0.5 mole) of cyanoguanidine ("dicyandiamide") and 50 g (0.5 mole) of 2,4-pentanedione ("acetylacetone") is heated at 120° C. for 15 hours. After the reaction mixture has cooled, 500 ml of water are added and the solution is acidified with hydrochloric acid at 0° C. to 10° C. The product thereby obtained as crystals is isolated by filtration with suction. 51.8 g (70% of theory) of 2-cyanoamino-4,6-dimethyl-pyrimidine of melting point 205° C. are obtained.

EXAMPLE (V-3)

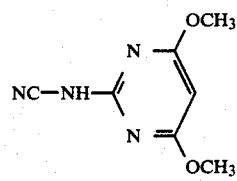

A solution, heated at 100° C., of 24 g (0.427 mole) of potassium hydroxide in 100 ml of water is added to a mixture of 9.2 g (0.043 mole) of 4,6-dimethoxypyrimidin-2-yl-thiourea and 70 ml of water at 100° C., with stirring. The mixture is subsequently stirred at 100° C. for 2 minutes and a solution, warmed to 100° C., of 16.2 g (0.05 mole) of lead-II acetate in 30 ml of water is then added. The mixture is heated under reflux for a further 5 minutes and is then cooled to 0° C. to 5° C., and 30 ml of glacial acetic acid are added to the aqueous solution. The product thereby obtained as crystals is isolated by filtration with suction.

6.3 g (81.5% of theory) of 2-cyanoamino-4,6-dimethoxy-pyrimidine of melting point 202° C. are obtained.

The compounds of the formula (V) listed in the following Table 5 can be prepared by the process described by way of example in the preceding example:

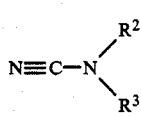

TABLE 5

| Example No. | R² | R³ | Melting point (°C.) |
|---|---|---|---|
| (V-4) | H | 2-(6-methyl-pyrimidinyl) | 203 (decomposition) |
| (V-5) | H | 2-(4,6-dimethyl-pyrimidinyl) | 258 |
| (V-6) | H | 2-(4-methoxy-6-N(C₂H₅)₂-pyrimidinyl) | 114 |
| (V-7) | H | 2-(4-SCH₃-6-NHC₂H₅-pyrimidinyl) | |
| (V-8) | H | 2-(4-OCH₃-6-NHCH₃-pyrimidinyl) | 210 |
| (V-9) | H | 2-(4,6-dimethyl-pyridinyl) | |
| (V-10) | H | 2-(4-Cl-6-N(C₂H₅)₂-pyrimidinyl) | 156 |
| (V-11) | H | 2-(4-methyl-5-COCH₃-pyrimidinyl) | 174 |
| (V-12) | H | 2-(4-methyl-5-COOC₂H₅-pyrimidinyl) | 126 |
| (V-13) | H | 2-(4-C₂H₅-pyrimidinyl) | 146 |
| (V-14) | H | 2-(4,6-dichloro-pyrimidinyl) | >250 |
| (V-15) | H | 2-(4-OCH₃-6-Cl-pyrimidinyl) | 200 |
| (V-16) | H | 2-(4-OCHF₂-6-CH₃-pyrimidinyl) | 174 |

TABLE 5-continued

| Example No. | R² | R³ | Melting point (°C.) |
|---|---|---|---|
| (V-17) | H | 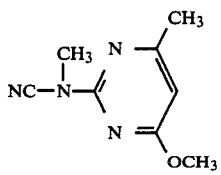 | 234 |
| (V-18) | H | (pyrimidine ring) | 186 |
| (V-19) | H | (4,6-diethoxy-pyrimidin-2-yl) | |
| (V-20) | H | (4,6-dimethyl-pyrimidin-2-yl with N at 3-position) | 232 |

2-(Alkyl-cyano-amino)-pyrimidines of the formula (V) can be prepared, for example, as follows:

Example (V-21)

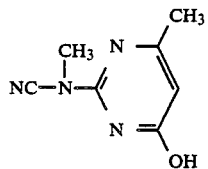

12.6 g (0.1 mole) of dimethyl sulphate are added dropwise to a solution of 15 g (0.1 mole) of 2-cyano-amino-4-hydroxy-6-methyl-pyrimidine and 4.1 g (0.1 mole) of sodium hydroxide in 60 ml of water, whereupon the reaction temperature rises from 20° C. to 40° C. After the mixture has been stirred at 20° C. for two hours, the product obtained as crystals is isolated by filtration with suction.

11.1 g (68% of theory) of 2-(methyl-cyano-amino)-4-hydroxy-6-methyl-pyrimidine of melting point 290° C. are obtained.

The following compound is obtained analogously:

Example (V-22)

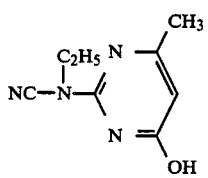

Melting point: 215° C. to 220° C.

Example (V-23)

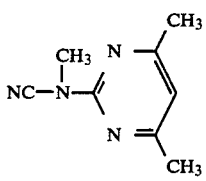

127.5 g (1 mole) of dimethyl sulphate are added dropwise to a solution of 75 g (0.5 mole) of 2-cyano-amino-4-hydroxy-6-methyl-pyrimidine—prepared according to process (b)—and 44 g (1.1 moles) of sodium hydroxide in 750 ml of water, the reaction temperature rising from 20° C. to 35° C. After the mixture has been stirred at 20° C. for twelve hours, the pH value is brought to between 9 and 10 by addition of sodium hydroxide solution and the product obtained as crystals is isolated by filtration with suction.

13 g (15% of theory) of 2-(methyl-cyano-amino)-4-methoxy-6-methyl-pyrimidine of melting point 123° C. are obtained.

The following compounds are obtained analogously:

Example (V-24)

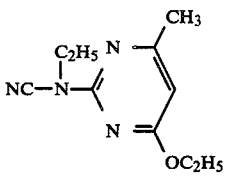

Melting point: 104° C.

Example (V-25)

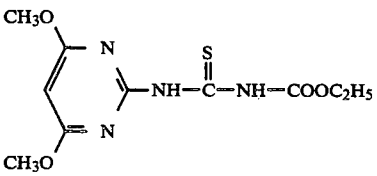

Melting point: 71° C.

PREPARATION OF THE STARTING SUBSTANCES OF THE FORMULA (XI)

Example (XI-1)

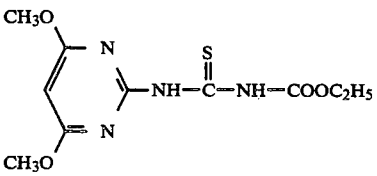

A mixture of 15.5 g (0.1 mole) of 2-amino-4,6-dimethoxy-pyrimidine, 13.1 g (0.1 mole) of ethoxycarbonyl isothiocyanate and 200 ml of acetonitrile is stirred at 60° C. for 2 hours. It is then cooled to 10° C. and the product obtained as crystals is isolated by filtration with suction.

22.5 g (79% of theory) of 1-(ethoxycarbonyl)-3-(4,6-dimethoxy-pyrimidin-2-yl)-thiourea of melting point 194° C. (decomposition) are obtained.

The compounds of the formula (XI) listed in the following Table 6 can be prepared by the process described by way of example in the preceding example:

$$R^7-\overset{O}{\underset{}{C}}-NH-\overset{S}{\underset{}{C}}-NH-R^3 \qquad (XI)$$

TABLE 6

| Example No. | R⁷ | R³ | Melting point (°C.) |
|---|---|---|---|
| (XI-2) | phenyl | 4,6-dimethoxy-pyrimidin-2-yl | 189 |
| (XI-3) | phenyl | 4-methyl-pyrimidin-2-yl | 198–9 (decomposition) |
| (XI-4) | —OC₂H₅ | 4-methyl-6-methoxy-pyrimidin-2-yl | 217 |
| (XI-5) | phenyl | 4-methyl-6-methoxy-pyrimidin-2-yl | 190 |
| (XI-6) | —OC₂H₅ | 4,6-dimethyl-pyridin-2-yl | 140 |
| (XI-7) | phenyl | 4,6-dimethyl-pyridin-2-yl | 145 |
| XI-8 | phenyl | 4-chloro-6-dimethylamino-pyrimidin-2-yl | 168 |

TABLE 6-continued

| Example No. | R⁷ | R³ | Melting point (°C.) |
|---|---|---|---|
| XI-9 | phenyl | 4-difluoromethoxy-6-methyl-pyrimidin-2-yl | 182 |
| XI-10 | —OC₂H₅ | 4-difluoromethoxy-6-methyl-pyrimidin-2-yl | 184–185 |
| XI-11 | —OC₂H₅ | 4,6-bis(difluoromethoxy)-pyrimidin-2-yl | 173 |
| XI-12 | —OC₂H₅ | 4-methoxy-6-chloro-pyrimidin-2-yl | 100 |
| XI-13 | phenyl | 4-ethoxy-6-methyl-pyrimidin-2-yl | 156 |
| XI-14 | phenyl | 4,6-diethoxy-pyrimidin-2-yl | 179 |
| XI-15 | —OC₂H₅ | 4,6-diethoxy-pyrimidin-2-yl | 159 |
| XI-16 | phenyl | pyrimidin-2-yl | 172–173 |

PREPARATION OF THE STARTING SUBSTANCES OF THE FORMULA (XII)

Example (XII-1)

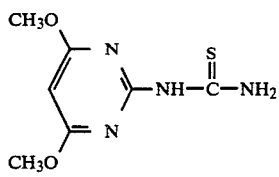

A mixture of 5.0 g (0.0175 mole) of 1-(ethoxy-carbonyl)-3-(4,6-dimethoxy-pyrimidin-2-yl)-thiourea, 4.0 g (0.1 mole) of sodium hydroxide and 100 ml of water is stirred at 20° C. for 2 days. Hydrochloric acid is then added dropwise, with stirring, until the solution has been rendered acid and the evolution of $CO_2$ has ended. The product obtained as crystals is isolated by filtration with suction.

3.5 g (94% of theory) of 4,6-dimethoxypyrimidin-2-yl-thiourea of melting point 245°–8° C. (decomposition) are obtained.

The compounds of the formula (XII) listed in the following Table 7 can be prepared by the process described by way of example in the preceding example:

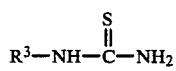

TABLE 7

| Example No. | $R^3$ | Melting Point (°C.) |
|---|---|---|
| (XII-2) | ![N-pyrimidinyl with CH3, CH3] | 264–265 (decomposition) |
| (XII-3) | ![N-pyrimidinyl with CH3, OCH3] | 205–207 (decomposition) |
| (XII-4) | ![N-pyrimidinyl with CH3, CH3] | 259–260 (decomposition) |
| XII-5 | ![N-pyrimidinyl unsubstituted] | 263 |
| XII-6 | ![N-pyrimidinyl with OCHF2, CH3] | 192–194 |

TABLE 7-continued

| Example No. | $R^3$ | Melting Point (°C.) |
|---|---|---|
| XII-7 | ![N-pyrimidinyl with Cl, OCH3] | 225–227 |
| XII-8 | ![N-pyrimidinyl with CH3, CH3] | 248 |
| XII-9 | ![N-pyrimidinyl with N(CH3)2, Cl] | |
| XII-10 | ![N-pyrimidinyl with OC2H5, OC2H5] | 166 |

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit urea being decisive. After three weeks, the degree of damage to the plants is rated in % damage in comparison to the development of the untreated control. The figures denote:

0% = no action (like untreated control)
100% = total destruction

In this test, the compound prepared according to Example 1 exhibits a very good herbicidal action.

It will be understood that the specification and examples are illustrative but not limitative of the present invention and that other embodiments within the spirit and scope of the invention will suggest themselves to those skilled in the art.

What is claimed is:

1. A process for the preparation of a 1-(2-oxyaminosulphonyl-phenylsulphonyl)-urea of the formula

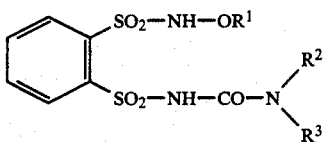

in which
R$^1$ is C$_1$–C$_{12}$-alkyl which is optionally substituted by fluorine, chlorine, cyano, C$_1$–C$_4$-alkoxy, C$_1$–C$_4$-alkylsulphonyl, C$_1$–C$_4$-alkyl-carbonyl, C$_1$–C$_4$-alkoxycarbonyl, C$_1$–C$_4$-alkyl-amino-carbonyl or di-(C$_1$–C$_4$-alkyl)-amino-carbonyl; or is C$_3$–C$_6$-alkenyl, C$_3$–C$_6$-alkinyl, C$_3$–C$_6$-cycloalkyl, C$_3$–C$_6$-cycloalkyl-C$_1$–C$_2$-alkyl; phenyl-C$_1$–C$_2$-alkyl which is optionally substituted by fluorine, chlorine, nitro, cyano, C$_1$–C$_4$-alkyl, C$_1$–C$_4$-alkoxy or C$_1$–C$_4$-alkoxy-carbonyl; or is phenyl which is optionally substituted by fluorine, chlorine, nitro, cyano, C$_1$–C$_4$-alkyl, trifluoromethyl, C$_1$–C$_4$-alkoxy, C$_1$–C$_2$-fluoroalkoxy, C$_1$–C$_4$-alkylthio, trifluoromethylthio or C$_1$–C$_4$-alkoxy-carbonyl, R$^2$ is hydrogen or C$_1$–C$_4$-alkyl which is optionally substituted by fluorine, chlorine, cyano, C$_1$–C$_4$-alkoxy, C$_1$–C$_4$-alkylthio, C$_1$–C$_4$-alkylsulphinyl, C$_1$–C$_4$-alkoxy-carbonyl, C$_1$–C$_4$-alkylamino-carbonyl or di-(C$_1$–C$_4$-alkyl)-amino-carbonyl; or is C$_3$–C$_6$-alkenyl, C$_3$–C$_6$-alkinyl; or phenyl-C$_1$–C$_2$-alkyl which is optionally substituted by fluorine, chlorine, nitro, cyano, C$_1$–C$_3$-alkyl, C$_1$–C$_4$-alkoxy or C$_1$–C$_4$-alkoxy-carbonyl, R$^3$ is the radical

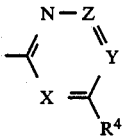

R$^4$ is hydrogen, fluorine, chlorine, bromine, hydroxyl; C$_1$–C$_4$-alkyl which is optionally substituted by fluorine and/or chlorine; C$_1$–C$_4$-alkoxy which is optionally substituted by fluorine and/or chlorine; C$_1$–C$_4$-alkylthio which is optionally substituted by fluorine and/or chlorine; amino, C$_1$–C$_4$-alkylamino or di-(C$_1$–C$_4$-alkyl)-amino, X is nitrogen or a methine bridge (CH),
Y is nitrogen or an optionally substituted methine bridge C—R$^5$,
R$^5$ is hydrogen, fluorine, chlorine, bromine or C$_1$–C$_4$-alkyl,
Z is nitrogen or an optionally substituted methine bridge C—R$^6$, and
R$^6$ is hydrogen, fluorine, chlorine, bromine, hydroxyl; C$_1$–C$_4$-alkyl which is optionally substituted by fluorine and/or chlorine; C$_1$–C$_4$-alkoxy which is optionally substituted by fluorine and/or chlorine; C$_1$–C$_4$-alkylthio which is optionally substituted by fluorine and/or chlorine; amino, C$_1$–C$_4$-alkylamino or di-(C$_1$–C$_4$-alkyl)-amino, comprising reacting water with a benzodisultam of the formula

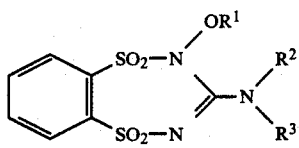

at a temperature between 0° C. and 100° C.

2. A process according to claim 1 wherein the reaction is effected in the presence of a diluent.

3. A process according to claim 1 wherein the reaction is effected in the presence of the base.

4. A process according to claim 1, in which
R$^1$ is C$_1$–C$_8$-alkyl which is optionally substituted by fluorine or chlorine; C$_3$–C$_4$-alkenyl, C$_1$–C$_2$-alkoxycarbonylmethyl; phenethyl or benzyl which is optionally substituted by fluorine, chlorine, nitro, cyano, methyl, methoxy or methoxy-carbonyl,
R$^2$ is hydrogen,
R$^3$ is the radical

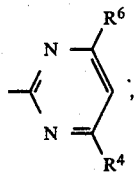

R$^4$ is chlorine, methyl, methoxy or ethoxy, and
R$^6$ is hydrogen, chlorine, methyl, methoxy, ethoxy, methylthio, ethylthio, dimethylamino or diethylamino.

* * * * *

UNITED STATES PATENT AND TRADEMARK OFFICE
CERTIFICATE OF CORRECTION

PATENT NO. : 4,658,027

DATED : April 14, 1987

INVENTOR(S) : Hans-Joachim Diehr, et al.

It is certified that error appears in the above-identified patent and that said Letters Patent is hereby corrected as shown below:

Col. 6, line 52      Delete "produces" and substitute --products--

Col. 8, line 11      Delete "solution" and substitute --solutions--

Col. 8, line 45      Correct --compare--

Col. 36, line 54      Delete "urea" and substitute --area--

Col. 37, line 34      Delete "$C_3$" and substitute --$C_4$--

Signed and Sealed this

First Day of September, 1987

Attest:

DONALD J. QUIGG

Attesting Officer      *Commissioner of Patents and Trademarks*